United States Patent [19]

Harbridge

[11] 4,342,749
[45] Aug. 3, 1982

[54] CLAVULANIC ACID DERIVATIVES A PROCESS FOR THEIR PREPARATION AND THEIR USE IN PHARMACEUTICAL COMPOSITIONS

[75] Inventor: John B. Harbridge, Coulsdon, England

[73] Assignee: Beecham Group Limited, England

[21] Appl. No.: 168,574

[22] Filed: Jul. 14, 1980

Related U.S. Application Data

[62] Division of Ser. No. 79,557, Sep. 27, 1979, Pat. No. 4,303,665.

[30] Foreign Application Priority Data

Oct. 27, 1978 [GB] United Kingdom ............... 42338/78

[51] Int. Cl.³ ...................... A61K 35/00; A61K 31/43
[52] U.S. Cl. .................................................... 424/114
[58] Field of Search ......................................... 424/114

[56] References Cited

PUBLICATIONS

Chemical Abstracts 89: 59890f (1978).

Primary Examiner—Jerome D. Goldberg
Attorney, Agent, or Firm—Jacobs & Jacobs

[57] ABSTRACT

Compounds of the formula (II):

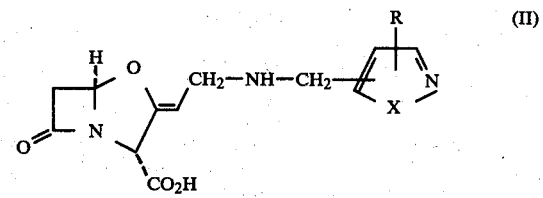

wherein X is sulphur or oxygen and R is hydrogen or alkyl of 1 to 3 carbon atoms, are useful for their antibacterial, β-lactamase inhibitory activity and synergistic activity when combined with a penicillin or cephalosporin.

24 Claims, No Drawings

CLAVULANIC ACID DERIVATIVES A PROCESS FOR THEIR PREPARATION AND THEIR USE IN PHARMACEUTICAL COMPOSITIONS

CROSS REFERENCE

This is a division of Ser. No. 079,557 filed Sept. 27, 1979, U.S. Pat. No. 4,303,665.

West Germany Offenlegungsschrift No: 2817085 discloses inter alia the compounds of the formula (I):

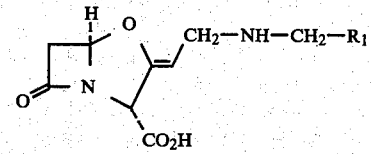

or an ester thereof wherein $R_1$ is a hydrogen atom, an alkyl group of up to 5 carbon atoms, a cycloalkyl group of 5 to 6 carbon atoms, a hydroxyalkyl group of up to 5 carbon atoms or a moiety of the sub-formula (a):

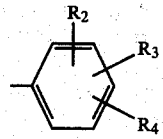

wherein $R_2$ is a hydrogen, fluorine, chlorine or bromine atom or an alkyl group of 1-3 carbon atoms, an alkoxyl group of 1-3 carbon atoms, an acyloxy group of 1-3 carbon atoms, a hydroxyl group, an alkyoxycarbonyl group containing 1-3 carbon atoms in the alkoxy part, or a group $-N(R_5)CO.R_6, -N(R_5)SO_2R_6$ or $-CO-NR_5R_6$ where $R_5$ is a hydrogen atom or an alkyl group of 1-3 carbon atoms or a phenyl or benzyl group and $R_6$ is an alkyl group of 1-3 carbon atoms or a phenyl or benzyl group; $R_3$ is a hydrogen, fluorine or chlorine atom or an alkyl group of 1-3 carbon atoms, an alkoxyl group of 1-3 carbon atoms or an acyloxy group of 1-3 carbon atoms; and $R_4$ is a hydrogen, fluorine or chlorine atom or an alkyl group of 1-3 carbon atoms or an alkoxyl group of 1-3 carbon atoms.

The present invention provides the compounds of the formula (II):

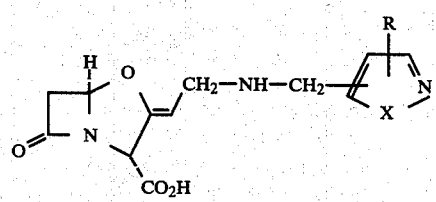

wherein X is a sulphur atom or an oxygen atom and R is a hydrogen atom or an alkyl group of 1-3 carbon atoms.

Since the compounds of the formula (II) exist as zwitterions they may also be represented by the formula (III), (IV), (V), (VI), (VII) and (VIII):

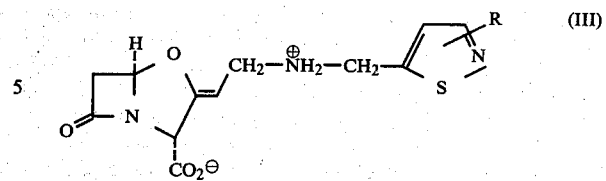

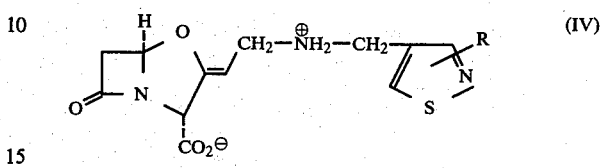

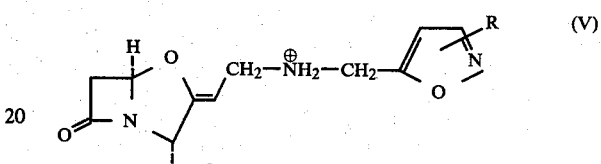

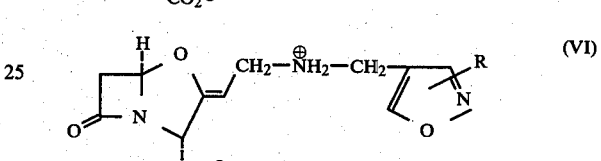

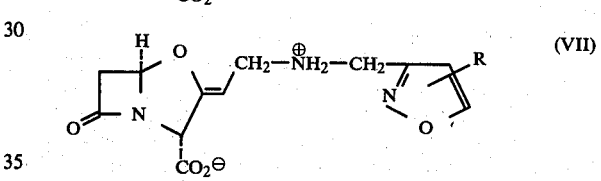

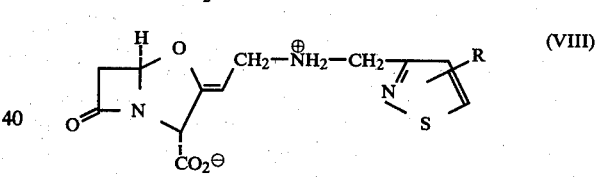

wherein R is as defined in relation to formula (II).

Favourably R is a hydrogen atom or a methyl group.

Aptly the compound of this invention is of the formula (III) or (V). Aptly the compound of this invention is of the formula (IV) or (VI). Aptly the compound of this invention is of the formula (VII) or (VIII).

A preferred compound is 9-isothiazol-5-ylaminodeoxyclavulanic acid.

The present invention also provides pharmaceutical compositions which comprise a compound of this invention and a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

Injectable or infusable compositions of a compound of the invention are particularly suitable as high blood levels of the compound can occur after administration by injection or infusion. Thus, one preferred composition aspect of this invention comprises a compound of the invention in sterile form and most suitably in sterile crystalline form. The zwitterionic compounds of this invention are particularly suitable for use in such compositions.

The injectable solution of the compound of this invention may be made up in a sterile pyrogen-free liquid such as water, aqueous ethanol or the like.

Compounds of this invention when in highly pure crystalline form tend to have relatively low aqueous solubilities so that if it is desired to administer substantial quantities of the medicament this can require fairly large quantities of water for reconstitution. In these circumstances it is often convenient to adminster the solution intravenously.

An alternative approach to administering the compounds of this invention is to utilise an injectable suspension. Such suspensions may be made up in sterile water, sterile saline or the like and may also contain suspending agents such as polyvinylpyrrolidone, lecithin or the like (for example in the manner described for amoxycillin trihydrate in Belgian Pat. No: 839109). Alternatively such compositions may be prepared in an acceptable oily suspending agent such as acharis oil or its equivalent.

Unit dose compositions comprising a compound of this invention adapted for oral administration form a further suitable composition aspect of this invention. Orally administrable compositions are of use as a synergistically effective blood levels can be expected at high doses and at lower doses such compositions may be used to treat infections localised in the gastro-intestinal tract.

Unit dose compositions comprising a compound of this invention adapted for topical administration are also presented by this invention. In this instance "topical administration" also includes local administration to internal surfaces of mammary glands of cattle, for example during the treatment of mastitis by intra-mammary administration.

The compound of the invention may be present in the composition as sole therapeutic agent or it may be present together with other therapeutic agents such as penicillin or a cephalosporin. Considerable advantages accrue from the inclusion of a penicillin or cephalosporin since the resulting composition shows enhanced effectiveness (synergy).

Penicillins suitable for inclusion in orally administrable compositions of this invention include benzylpenicillin, phenoxymethylpenicillin, propicillin, amoxycillin, ampicillin, epicillin, cyclacillin and other orally active penicillins and their pharmaceutically acceptable salts and in-vivo hydrolysable esters and aldehyde and ketone adducts of those penicillins containing a 6-α-aminoacylamino side chain and their pharmaceutically acceptable salts. Suitable penicillin in-vivo hydrolysable esters include the acetoxymethyl, pivaloyloxymethyl, α-ethoxycarbonyloxyethyl and phthalidyl esters of ampicillin or amoxycillin or the phenyl, tolyl and indanyl α-esters of carbenicillin and ticarcillin and pharmaceutically acceptable salts thereof. Suitable aldehyde and ketone adducts of penicillins containing a 6-α-aminoacylamino side chain include the formaldehyde and acetone adducts of ampicillin and amoxycillin such as metampicillin and hetacillin and their salts. Suitable penicillins for inclusion in injectably or infusably administrable compositions include the pharmaceutically acceptable salts of benzylpenicillin, phenoxymethylpenicillin, carbenicillin, propicillin, ampicillin, amoxycillin, epicillin, ticarcillin and cyclacillin.

Cephalosporins suitable for inclusion in orally administrable compositions of this invention include cephalexin, cephradine, cephaloglycine and their pharmaceutically acceptable salts and other known cephalosporins and their pharmaceutically acceptable salts and in-vivo hydrolysable esters and aldehyde and ketone adducts of those cephalosporins containing a 7-α-aminoacylamino side chain and their pharmacetically acceptable salts. Suitable cephalosporins for inclusion in the injectable or infusable compositions of this invention include the pharmaceutically acceptable salts of cephaloridine, cephalothin, cefazolin, cephalexin, cephacetrile, cephamandole, cephaprinin, cephradine, cephaloglycine and other known cephalosporins.

When present in a pharmaceutical composition together with a penicillin or cephalosporin, the weight ratio of synergist or its salt present to penicillin or cephalosporin present may be from, for example 3:1 to 1:10 for example 1:1 to 1:4.

Suitably the weight of the compound of this invention in a unit dosage form of this invention will be from 50 to 500 mg and more suitably from 50 to 250 mg.

In general the total quantity of antibacterial agents present in a synergistic composition of this invention will not be greater than 1500 mg and will usually be between 100 and 1000 mg.

Normally between 500 and 3000 mg of the synergistic compositions of the invention will be administered each day of treatment (to an average 70 kg adult). However, for the treatment of severe systemic infections or infections of particularly intransigent organisms, higher doses may be used in accordance with clinical practice.

One particularly favoured composition of this invention will contain from 150 to 1000 mg of amoxycillin as the trihydrate or sodium salt and from 25 to 500 mg of a compound of this invention.

A further particularly favoured composition of this invention will contain from 150 to 1000 mg of ampicillin or a pro-drug therefor and from 25 to 500 mg of a compound of this invention.

Most suitably this form of composition will contain ampicillin trihydrate, ampicillin anhydrate, sodium ampicillin, hetacillin, pivampicillinhydrochloride, bacampicillin hydrochloride or talampicillin hydrochloride.

Most suitably the preceding compositions will contain from 200 to 700 mg of the penicillin component. Most suitably the preceding composition will comprise from 50 to 250 mg of a compound of the formula (III) to (VIII) in crystalline form.

Another particularly favoured composition of this invention will contain from 200 to 2000 mg of carbenicillin, ticarcillin or a pro-drug therefor and from 50 to 500 mg of a compound of the invention.

Suitably this form of composition will contain di-sodium carbenicillin. Suitably this form of the composition will contain di-sodium ticarcillin.

More suitably this form of the composition will contain from 75 to 250 mg of a compound of the formulae (III)–(VIII) in crystalline form.

The present invention also provides a method of treating bacterial infections in humans or domestic mammals which comprises the administration of a composition of this invention.

Commonly the infection treated will be due to a strain of *Staphylococcus aureus, Klebsiella aerogenes, Escherichia coli*, Proteus sp. or the like. The organisms believed to be most readily treated by an antibacterially effective amount of a compound of this invention is *Staphylococcus aureus*. The other organisms named are more readily treated by using a synergistically effective amount of the compound of the invention and a penicillin or cephalosporin. The administration of the two components may take place separately but in general we prefer to use a composition containing both the synergist and the penicillin or cephalosporin.

The indications for treatment include respiratory tract and urinary tract infections in humans and mastitis in cattle.

The present invention also provides a process for the preparation of a compound of the formula (II) which process comprises the reduction with a water soluble complex hydride of a salt of a compound of the formula (IX):

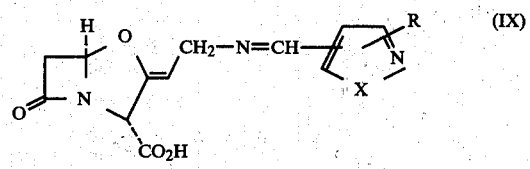

wherein X and R are as defined in relation to formula (II).

Suitable water soluble complex hydrides include borohydrides such as lithium borohydride, sodium borohydride, sodium cyanoborohydride, potassium borohydride or the like. In general an excess of the hydride is employed.

The reaction is carried out in an aqueous medium, for example in water or in a mixture of water with an inert water-miscible organic solvent such as tetrahydrofuran, dioxan or the like.

It is a favoured feature of this invention that ambient and near ambient temperatures may be employed, for example the reaction may be carried out at a temperature of from 0° to 30° and conveniently at ambient, for example at about 18°–25°.

The pH of the reaction is best kept below 10 and this may be effected by the addition of an acid such as hydrochloric or like mineral acid simultaneously with the complex hydride. This may be carried out in a pH-stat or other similar system.

Once the reaction is over it is advantageous to return the pH to about 5–8.

The desired product may be obtained from the reaction mixture by evaporation of the solvent. Purification may be effected by crystallisation (for example before all the solvent has been evaporated off) or by column chromatography, for example using silica gel or cellulose and butanol/ethanol/water 4/4/1.

The compounds of the formula (IX) are novel and as such form an aspect of this invention.

The present invention also provides a process for the preparation of a compound of the formula (IX) which process comprises the reaction of 9-aminodeoxyclavulanic acid with a compound of the formula (X):

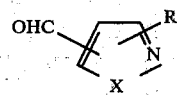

wherein X and R are as defined in relation to formula (II), in an aqueous solvent wherein the solution is maintained at an alkaline pH.

The pH of the solution is most suitably maintained in the region of 7–10 and preferably 8–9. This may be effected by the addition of base such as an alkali or alkaline earth metal hydroxide, a carbonate or bicarbonate or with a strong organic base which is unreactive towards aldehydes. Thus suitable bases include lithium hydroxide, sodium hydroxide, potassium hydroxide, calcium hydroxide, barium hydroxide, sodium carbonate, potassium bicarbonate, triethylamine and the like. It is convenient to add the base automatically, for example in a pH-stat.

Solvents suitable for use in this process include water and water in a mixture with inert water miscible organic solvents such as tetrahydrofuran, dioxan, dimethylformamide and the like.

The temperature under which this reaction proceeds in convenient in that it is at or near ambient for example 0°–30° C. and more suitably 18°–25° C.

Most suitably an excess of the aldehyde is present, for example a 2–10 fold excess.

The compound of the formula (IX) is generally only stable in the presence of excess of the aldehyde. For this reason, and for general convenience, it is preferred to form and use the compound of the formula (IX) in situ. This adds to the commercial attractiveness of this overall process for the preparation of the compounds of the formula (II).

9-Aminodeoxyclavulanic acid, its preparation and its use are described in co-pending United States patent application Ser. No. 900,451, and in French Publication No. 2353556.

The following Example illustrates the invention.

EXAMPLE 1

9-Isothiazol-5-yl-aminodeoxyclavulanic Acid

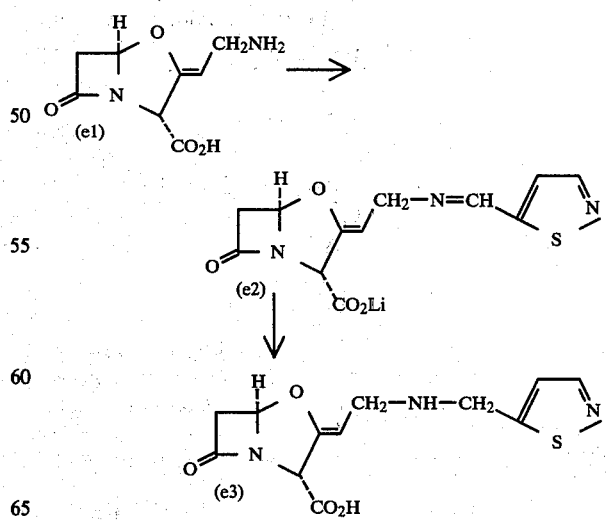

To a stirred solution of 9-aminodeoxyclavulanic acid (e1) (0.2 g) in water (10 ml) and tetrahydrofuran (10 ml)

was added isothiazole-5-carboxaldehyde (0.5 ml). The pH was maintained constant at 8.3 by the addition of lithium hydroxide solution (1 M). The theoretical amount was taken up (1 ml). At this point the solution contained the Schiffs base (e2). The pH of the solution was increased to 9, and sodium borohydride (0.2 g) was added in small portions during 15 mins, maintaining the pH of the solution between 9 and 10 (mostly about 9.2) by the simultaneous addition of 1 M HCl. T.l.c. then showed that a new zone with Rf slightly higher than the primary amine had appeared ($SiO_2$-butanol/isopropanol/water-7:7:6). The reaction mixture was evaporated to dryness, and extracted with ethyl acetate (2×25 ml). The insoluble material was dissolved in water (about 2 ml) and subjected to column chromatography on silica gel using butanol/isopropanol/water, 7:7:6, as the elution solvent. Fractions containing the required product (by t.l.c) were combined and evaporated to a colourless crystalline solid, which was triturated with acetone (20 ml), filtered off, washed with ether and dried in air, to yield 9-isothiazol-5-ylaminodeoxyclavulanic acid (e3) (0.18 g).

I.r (nujol mull) 2500–3800 (broad, with fine structure), 1808, 1693, 1615 and 1575 $cm^{-1}$.

Demonstration of Activity

The minimum inhibitory concentration (MIC) of ampicillin alone and in combination with 9-isothiazol-5-ylaminodeoxyclavulanic acid was determined using a standard microtitre technique.

|  |  | Staph. aureus Russell | Kleb aerogenes E 70 | E. Coli JT39 |
|---|---|---|---|---|
| Ampicillin alone |  | 1000 | 125 | 2000 |
| Ampicillin + 9-isothiazol-5-ylaminodeoxy-clavulanic acid | 1.0 $\mu gmL^{-1}$ | 0.15 | 3.1 | 8 |
|  | 5.0 $\mu gmL^{-1}$ | — | 1.6 | 2 |
| 9-Isothiazol-5-ylamino-deoxyclavulanic acid alone |  | 4.0 | 31 | 31 |

What we claim is:

1. A pharmaceutical composition useful for treating bacterial infections in mammals including humans which comprises at least a synergistically effective amount of a compound of the formula (II):

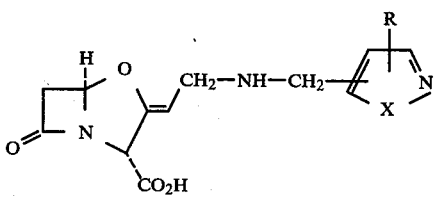

wherein X is sulphur or oxygen and R is hydrogen or alkyl of 1 to 3 carbon atoms, and an antibacterially effective amount of amoxycillin, a pharmaceutically acceptable salt thereof or an in vivo hydrolyzable ester thereof, in combination with a pharmaceutically acceptable carrier.

2. A composition according to claim 1 wherein the ratio of the compound of the formula (II) to amoxycillin, a pharmaceutically acceptable salt thereof or an in vivo hydrolyzable ester thereof, is 3:1 to 1:10.

3. A composition according to claim 2 wherein the ration is 1:1 to 1:4.

4. A composition according to claim 1 wherein the compound is of the formula (III), (IV), (V), (VI), (VII) or (VIII)

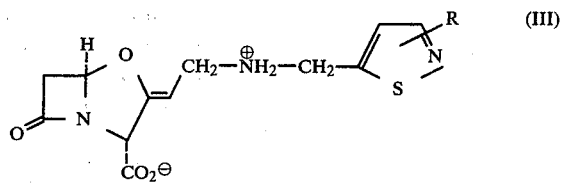

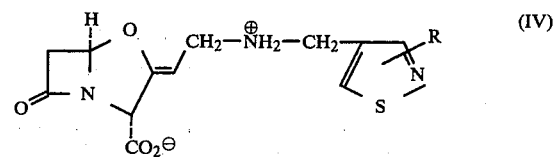

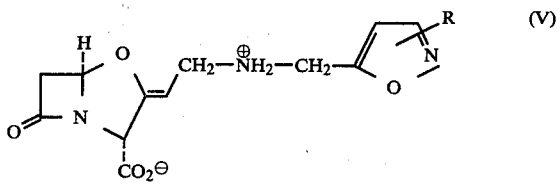

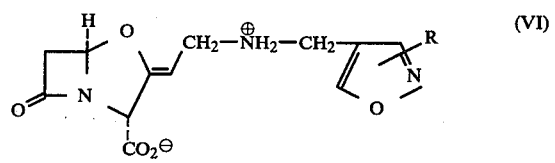

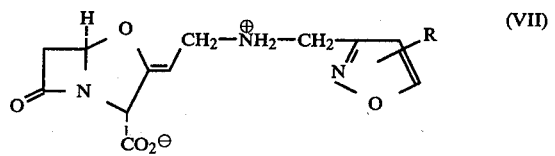

or

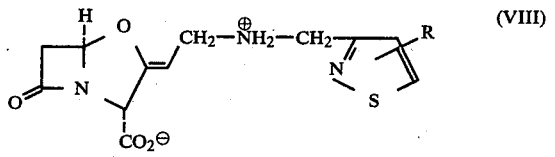

wherein R is hydrogen or alkyl of 1 to 3 carbon atoms.

5. A composition according to claim 1 wherein R is hydrogen or methyl.

6. A composition according to claim 4 wherein R is hydrogen or methyl.

7. A composition according to claim 1 wherein the compound is 9-isothiazol-5-methylaminodeoxyclavulanic acid.

8. A composition according to claim 1 in oral administration form.

9. A composition according to claim 1 in parenteral administration form.

10. A composition according to claim 1 in injectible administration form.

11. A composition according to claim 1 in a form suitable for infusion.

12. A composition according to claim 1 in a form suitable for topical application.

13. A method treating bacterial infections in humans and animals which comprises administering to a human or animal in need thereof at least a synergistically effective amount of a compound of the formula (II):

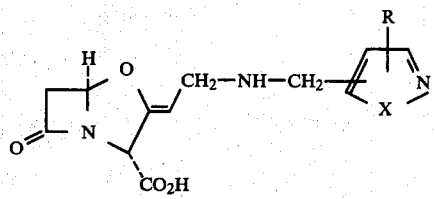
(II)

wherein X is sulphur or oxygen and R is hydrogen or alkyl of 1 to 3 carbon atoms, and an antibacterially effective amount of amoxycillin, a pharmaceutically acceptable salt thereof or an in vivo hydrolyzable ester thereof, in combination with a pharmaceutically acceptable carrier.

14. A method according to claim 13 wherein the ratio of compound of the formula (II) to amoxycillin, a pharmaceutically acceptable salt thereof or an in vivo hydrolyzable ester thereof, is 3:1 to 1:10.

15. A method according to claim 14 wherein the ratio is 1:1 to 1:4.

16. A method according to claim 13 wherein the compound is of the formula (III), (IV), (V), (VI), (VII) or (VIII):

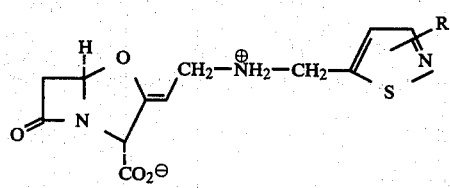
(III)

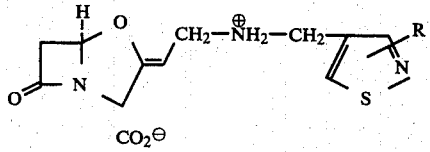
(IV)

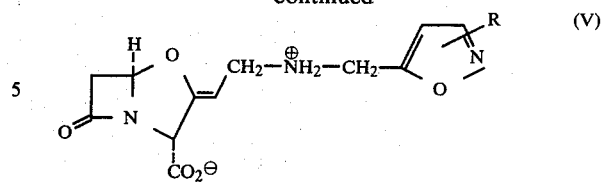
(V)

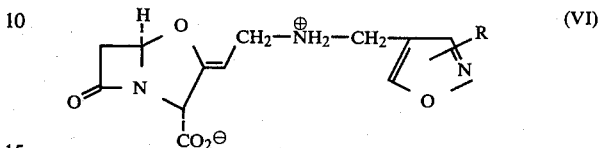
(VI)

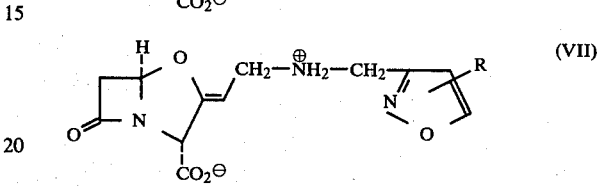
(VII)

or

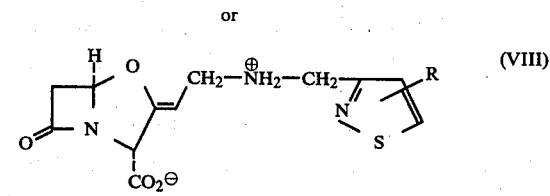
(VIII)

wherein R is hydrogen or alkyl of 1 to 3 carbon atoms.

17. A method according to claim 13 wherein R is hydrogen or methyl.

18. A method according to claim 16 wherein R is hydrogen or methyl.

19. A method according to claim 13 wherein the compound is 9-isothiazol-5-yl-methylaminodeoxyclavulanic acid.

20. A method according to claim 13 wherein the administration is oral.

21. A method according to claim 13 wherein the administration is parenteral.

22. A method according to claim 13 wherein the administration is by injection.

23. A method according to claim 13 wherein the administration is by infusion.

24. A method according to claim 13 wherein the administration is by topical application.

* * * * *